United States Patent [19]

Stahl-Rees

[11] Patent Number: 5,610,075

[45] Date of Patent: Mar. 11, 1997

[54] COMPETITIVE ELECTROCHEMILUMINESCENCE ASSAYS FOR ENDOTOXINS USING A RUTHENIUM LABEL

[76] Inventor: Marianne Stahl-Rees, The Hermitage, Sharpstone, Freshford, Bath BA3 6DA, United Kingdom

[21] Appl. No.: 373,365

[22] Filed: Jan. 17, 1995

[51] Int. Cl.$^6$ .................................................. G01N 33/53
[52] U.S. Cl. ........................... 436/501; 436/149; 514/15; 422/52
[58] Field of Search ................................... 514/21, 12, 15, 514/8; 530/328; 435/7.9; 436/531; 525/54.1; 424/92, 85.5, 534; 210/638

[56] References Cited

U.S. PATENT DOCUMENTS

| | | | |
|---|---|---|---|
| 4,755,382 | 7/1988 | Flaherty | 424/92 |
| 4,803,072 | 2/1989 | Dalton et al. | 424/85.5 |
| 4,808,314 | 2/1989 | Karplus et al. | 210/638 |
| 5,059,654 | 10/1991 | Hou et al. | 525/54.1 |
| 5,061,445 | 10/1991 | Zoski et al. | 422/52 |
| 5,068,088 | 11/1991 | Hall et al. | 422/52 |
| 5,089,274 | 2/1992 | Marra et al. | 424/534 |
| 5,093,268 | 3/1992 | Leventis et al. | 436/172 |
| 5,126,276 | 6/1992 | Fish | 436/531 |
| 5,147,806 | 9/1992 | Kamin et al. | 436/149 |
| 5,171,739 | 12/1992 | Scott et al. | 514/12 |
| 5,177,059 | 1/1993 | Handley et al. | 514/8 |
| 5,221,605 | 6/1993 | Bard et al. | 435/4 |
| 5,234,912 | 8/1993 | Marra et al. | 514/21 |
| 5,238,808 | 8/1993 | Bard et al. | 435/4 |
| 5,247,243 | 9/1993 | Hall et al. | 324/71.1 |
| 5,296,191 | 3/1994 | Hall et al. | 422/52 |
| 5,308,834 | 5/1994 | Scott et al. | 514/12 |
| 5,310,687 | 5/1994 | Bard et al. | 436/518 |
| 5,316,911 | 5/1994 | Baek | 435/7.9 |
| 5,334,584 | 8/1994 | Scott et al. | 514/12 |
| 5,358,933 | 10/1994 | Porro | 514/15 |
| 5,371,186 | 12/1994 | Porro | 530/328 |

OTHER PUBLICATIONS

Morrison, D. et al., Immunochem. 1976, vol. 13, pp. 813–818, Binding of Polymyxin B to the Lipid A Portion of Bacterial Lipo Polysaccharide.

Primary Examiner—James C. Housel
Assistant Examiner—Ginny Allen Portner
Attorney, Agent, or Firm—John W. Ryan; Patrick J. Igoe

[57] ABSTRACT

This invention is directed to a process for performing a competitive, electrochemiluminescence assay for endotoxins. In particular, the invention involves the use of ruthenium (II)tris-bipyridine NHS ester label to detect the labeled endotoxins.

10 Claims, No Drawings

COMPETITIVE ELECTROCHEMILUMINESCENCE ASSAYS FOR ENDOTOXINS USING A RUTHENIUM LABEL

FIELD OF THE INVENTION

This invention relates to the development of an electrochemiluminescence (ECL) based assay the detection and quantification of endotoxins (e.g., lipopolysaccharides, LPS) labeled with ruthenium (II)tris-bipyridine NHS ester. More particularly, this invention relates to the detection and quantitation of endotoxins in aqueous solution.

BACKGROUND OF THE INVENTION

Electrochemiluminescence is well-described in U.S. Pat. Nos. 5,061,445; 5,068,088; 5,093,268; 5,147,806; 5,221,605; 5,238,808; 5,247,243; 5,296,191; and 5,310,687. Each of these patents is incorporated herein by reference. Nevertheless, the assay formats themselves (, e.g., for endotoxins) require novel and unobvious approaches to problems in the newly emerging field of electrochemiluminescence.

The only known assay for endotoxins is an FDA-approved assay on the market known as the LAL (Limulus Amebocyte Lysate) Test. This test takes 2 days and the reproducibility of the assay is not very good to the average practitioner. It is desirable to improve the assay so that it is less labor intensive and more reproducible. The present invention overcomes the first problem and has a great potential to overcome the second problem with reproducibility.

Endotoxins or lipopolysaccharides (LPS) are complex, amphiphatic macromolecules that comprise three genetically, biochemically, and antigenically distinct domains referred to as the O-side chain, core oligosaccharide, and lipid A. The LPS core structure, consisting of the core oligosaccharide and lipid A, is relatively conserved among different species. This observation, in addition to the knowledge that many biological activities of LPS reside in the lipid A moiety, is important when considering any modification and derivatization of the LPS molecule.

The present invention protects the lipid A as well as the core oligosaccharide structure, during labeling with the ruthenium (II) tris-bipyridine NHS ester, referred to as the TAG-label hereafter. LPS structures with ethanolamine groups are selected for labeling since they contain amino groups to which the TAG-label reacts. Ethanolamine-containing lipopolysacchrides also have these groups in the biologically important lipid A portion and in the core structure.

The TAG-labeled material is then used to develop a sensitive, reproducible, and fast detection method for endotoxins in aqueous solutions using the ORIGEN™ Analyzer to detect the electrochemiluminescence originating from the TAG-label in contact with an electrode in the aforementioned instrument.

SUMMARY OF THE INVENTION

The present invention provides a novel assay for carrying out a competitive, electrochemiluminescence assay for endotoxins. In accordance with one aspect of the present invention, the TAG-labeling procedure is performed in the presence of polymyxin B, which is known to bind to the lipid A portion of endotoxins. This is to protect the biologically relevant part of the endotoxin, which also contains the aminogroups that the TAG-NHS ester potentially could react with, during the coupling reaction. Polymyxin B is a cyclic amphipathic peptide antibiotic that contains free amino groups derived from $\alpha,\gamma$-diaminobutyric acid and a fatty acid tail.

A competitive assay is then set up for the detection of endotoxins in aqueous solution. This assay is developed on the ORIGEN Analyzer.

The existing TAG-labeling protocol has been modified to overcome the problems with TAG-labeling of endotoxins (amino groups in the biologically active region). New features include: TAG-labeling in the presence of a protecting molecule, in this case polymyxin B; the separation of the TAG-labeled endotoxin-polymyxin B complex from free TAG-label using a Protein A column; the breakup of the TAG-labeled endotoxin-polymyxin B complex using 5% 1-propanol; and the utilization of the TAG-labeled endotoxin in a competitive assay whereby TAG-labeled endotoxin is competing with sample endotoxins for the binding to the biotinylated polymyxin B, which is subsequently captured on Streptavidin magnetic beads.

In accordance with another aspect of the present invention, a TAG-labeling procedure exists for the labeling of free amines on proteins, peptides, etc. This protocol does not take into consideration molecules that do not exhibit free amines as such. Also, the existing protocol fails to recommend other purification methods to separate bound TAG-label from free. The invention described herein has made the following improvements to the TAG-labeling protocol:

1. The TAG-labeling of a molecule in the presence of another molecule protects the biologically important part of the molecule to be labeled from being modified by the labeling procedure.

2. The separation of bound from free TAG-label is performed on a Protein A column which binds endotoxins (in the presence of 150 mM NaCl).

3. The separation of the protecting molecule from the now TAG-labeled endotoxins is accomplished with chaotropic agents (1-propanol).

4. The separation of the now free TAG-labeled endotoxin from the protecting molecule is done by using a Protein A column (in the presence of 5% 1-propanol and 150 mM NaCl).

DETAILED DESCRIPTION OF THE INVENTION

The following specifically describes the TAG-labeling protocol and the results obtained in a competitive assay using the ORIGEN Analyzer as the detection system for the produced electrochemiluminescence:

1. Polymyxin B is added to endotoxin on a molar ratio of 10:1 in PBS pH 7.2 containing 150 mM NaCl.

2. TAG-NHS-ester is added to the mixture on a molar ratio of 20:1. The TAG-label is first dissolved in DMSO.

3. The coupling reaction is allowed to proceed for 3 h at room temperature in the dark. This results in a TAG-labeled endotoxin—polymyxin complex.

4. Separation of bound TAG-label from free was performed on a Protein A column in PBS pH 7.2 in the presence of 150 mM NaCl. Without either sodium ions or calcium ions the endotoxin does not bind to Protein A. The size of the column was 0.5×5 cm for the purification of 2 mg of endotoxin.

5. TAG-labeled endotoxin was freed from the Polymyxin B interaction by incubation for 1.5 hours in PBS pH 7.2 with 5% 1-propanol. Incubation in 1M NaCl failed to remove the Polymyxin B molecules probably due to the nature of the binding interaction which is primarily hydrophobic.

6. Polymyxin B was biotinylated using the biotin ester.

7. Biotinylated polymyxin B was mixed with TAG-labeled endotoxin, or with an increasing amount of endotoxin standard (*E. coli* 011:B4) and incubated for 1 hour at room temperature after which the ECL Signal was read.

8. Experiments 1 and 2 were performed with a TAG-labeled endotoxin that had been separated from the polymyxin B using 1M NaCl 11.5 hours; the last experiment was performed using 5% 1-propanol to separate the TAG-labeled endotoxin from the polymyxin B.

First Experiment

Added "cold" endotoxins at a concentration in the region of pg/ml did not alter the ECL signal.

Second Experiment

When the concentration of endotoxin was increased to the ng level, where the lowest concentration of added endotoxin was 1 ng/ml, did give a decrease in the ECL Signal (from 8014 to 5667).

Third Experiment

Finally, a sensitivity of 0.1 ng/ml was achieved (ECL 20988 dropped to 11057).

Other molecules apart from polymyxin B could be used in this assay to serve as molecules that protect the endotoxin during the coupling reaction to the TAG-label. Three specific examples of these other molecules are BPI (bacterial permeability increasing protein, 55 kDa); Protein A; and LPS-binding protein (60 kDa).

The examples provided above are provided for illustration purposes only. They are not intend to limit the scope of protection for applicant's invention. Accordingly, it is understood that the full scope of applicant's invention is set forth in the attached claims.

We claim:

1. A process for performing a competitive electrochemiluminescence assay for endotoxins, comprising the steps of:
   (a) protecting the lipid A portion of the endotoxins with a protective molecule;
   (b) labeling endotoxin with ruthenium (II) tris-bipyridine NHS ester (TAG) to obtain TAG-labeled endotoxin;
   (c) separating the TAG-labeled endotoxins from the protective molecule;
   (d) derivatizing polymyxin B with biotin ester to obtain biotinylated polymyxin B;
   (e) mixing the biotinylated polymyxin B with the TAG-labeled endotoxin and with sample endotoxin so that the TAG-labeled endotoxin and the sample endotoxin compete with each other for binding to the biotinylated polymyxin B and allowing incubation to proceed in the resulting mixture;
   (f) exposing the resulting mixture to electrochemical energy to thereby cause electrochemiluminescence; and
   (g) measuring the electrochemiluminescence and determining from said measurement the amount of sample endotoxin.

2. A process for performing a competitive, electrochemiluminescence assay for endotoxins, comprising the steps of:
   (a) protecting the lipid A portion of the endotoxins with a protective molecule;
   (b) subsequently labeling the protected endotoxins with ruthenium (II) tris-bipyridine NHS ester (TAG);
   (c) separating the TAG-labeled endotoxins from the protective molecule,
   (d) derivatizing the protective molecule so that it is biotinylated;
   (e) mixing the biotinylated protective molecule with the TAG-labeled endotoxin and the sample endotoxin compete with each other for binding to the biotinylated protective molecule and allowing incubation to proceed in the resulting mixture;
   (f) exposing the resulting mixture to electrochemical energy to thereby cause electrochemiluminescence; and
   (g) measuring the electrochemiluminescence and determining from said measurement the amount of sample endotoxin.

3. The process of claim 2, wherein said protective molecule is a cyclic amphipathic peptide antibiotic.

4. The process of claim 2, wherein said protective molecule is polymyxin B.

5. The process of claim 2, wherein said TAG is first dissolved in DMSO before addition to said protected endotoxins.

6. The process of claim 2, wherein the labeling of said protected endotoxins proceeds for 3 hours at room temperature in the dark.

7. The process of claim 2, wherein the separation of TAG-labeled endotoxins from the protective molecule is performed by incubation for 1.5 hours in PBS at pH 7.2 with 5% 1-propanol.

8. The process of claim 2, wherein said TAG is first dissolved in DMSO before addition to said protected endotoxins.

9. The process of claim 2, wherein the labeling of said protected endotoxins proceeds for 3 hours at room temperature in the dark.

10. The process of claim 2, wherein the separation of TAG-labeled endotoxins from the protective molecules is performed by incubation for 1.5 hours in PBS at pH 7.2 with 5% 1-propanol.

* * * * *